United States Patent [19]

Cox

[11] Patent Number: 4,471,776

[45] Date of Patent: Sep. 18, 1984

[54] STATIC TRACHEOSTOMY TUBE

[76] Inventor: Everard F. Cox, 4510 Mt. Carmel Rd., Hampstead, Md. 21074

[21] Appl. No.: 360,026

[22] Filed: Mar. 19, 1982

Related U.S. Application Data

[63] Continuation of Ser. No. 214,243, Dec. 8, 1980, Pat. No. 4,340,046.

[51] Int. Cl.³ .......................................... A61M 16/00
[52] U.S. Cl. .......................... 128/207.15; 128/207.17
[58] Field of Search ...................... 128/207.14, 207.15, 128/207.16, 207.17, 200.26; 24/115 G, 263 R, 205.14 K; 49/477; 138/93, 113; 604/96, 97, 98, 99, 100, 101, 102, 103

[56] References Cited

U.S. PATENT DOCUMENTS

| | | | |
|---|---|---|---|
| 2,923,299 | 2/1960 | Blackwood | 128/207.17 |
| 3,348,542 | 10/1967 | Jackson | 604/96 |
| 3,372,439 | 3/1968 | Schmid | 24/263 R |
| 3,599,642 | 8/1971 | Tindel | 128/207.14 |
| 3,693,624 | 9/1972 | Shiley et al. | 128/207.15 |
| 3,760,811 | 9/1973 | Andrew | 128/207.17 |
| 3,810,474 | 5/1974 | Cross | 128/207.15 |
| 3,858,615 | 1/1975 | Weigl | 128/204.18 |
| 4,064,882 | 12/1977 | Johnson et al. | 128/207.15 |
| 4,278,081 | 7/1981 | Jones | 128/207.15 |

FOREIGN PATENT DOCUMENTS

| | | | |
|---|---|---|---|
| 7965 | 3/1899 | United Kingdom | 138/93 |

Primary Examiner—Henry J. Recla
Attorney, Agent, or Firm—Walter G. Finch

[57] ABSTRACT

The invention is an improved tracheostomy tube for providing a reliable airway for patients requiring mechanical assistance in breathing, without the complications of prolonged tracheostomy that are present in current tracheostomy tube devices. The present invention makes tracheostomy a safer modality of care with four distinctive features in the configuration. The four distinctive features are (1) a precision cuff fitted to each trachea; (2) a flexible tube that will conform to any depth of the trachea within the neck; (3) a self-locking clip that adjusts the tube securely to any neck regardless of the depth of the trachea; and (4) a malleable but rigid obturator for ease of insertion. These four features comprise the structure of the improved tracheostomy tube, being (1) a flexible tube, (2) an encircling pressure cuff, (3) a removably insertable malleable obturator, and (4) a self-locking neck plate to secure the tube to the neck.

6 Claims, 10 Drawing Figures

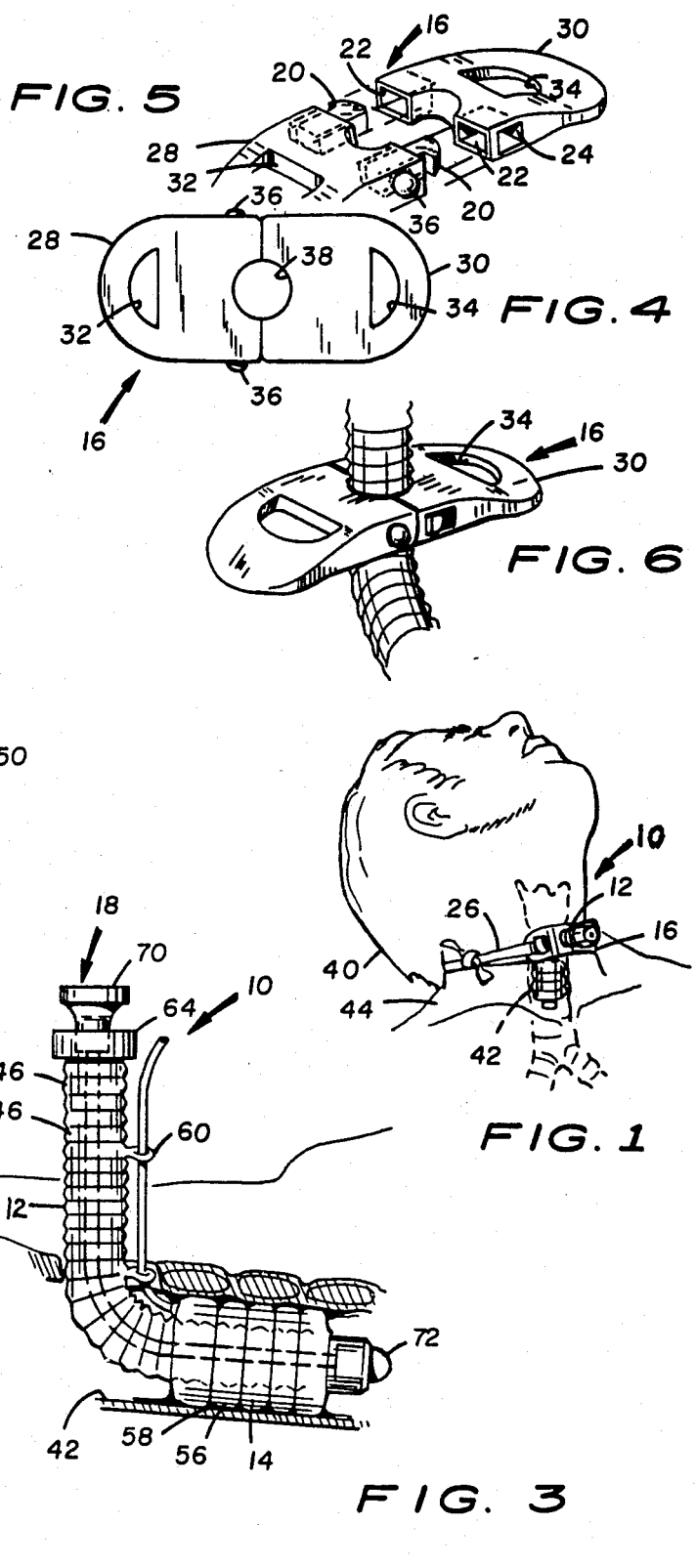

STATIC TRACHEOSTOMY TUBE

This is a continuation of application Ser. No. 214,243, filed Dec. 8, 1980 and now U.S. Pat. No. 4,340,046.

BACKGROUND AND SUMMARY OF THE INVENTION

The invention relates to medical and surgical devices and in particular to medical and surgical devices used in conjunction with patient breathing problems. Specifically, the invention relates to tracheostomy, an operation for providing an airway for patients requiring mechanical assistance in breathing, and for conduction of anesthetic gas when the tube is placed in the trachea through the mouth or nose.

At present, the size (both calibre and length), the shape, and the overall construction of the standard tracheostomy tubes that are in use are somewhat traditional, being almost identical with that found illustrated in Mackensie's book which was published in 1880.

Initially, the tracheostomy was used almost exclusively to divert the air from an obstruction of the larynx, regardless of the cause. The tracheostomy tube was a rigid device and remains so today. With the advent of closed systems of ventilatory support used in anesthesia, an inflatable cuff was added to the device.

Recently, the tracheostomy has become critical to modern respiratory care and it is more than just an airway, it is the conduit of survival when attached to a mechanical ventilator. The effectiveness, however, is often negated by complications that are associated with the tracheostomy tubes that are in use at this time.

Among those patients requiring tracheostomy there are anatomical variations of the depth of the trachea within the neck. These differences are seen in the long neck and in the short heavy neck.

Because deviations from normal anatomical conditions are common, placing one of the currently available rigid tracheostomy tubes into a proper and a constant aligned position within the tracheal lumen becomes virtually impossible. The lack of flexibility in adjusting a tracheostomy tube to each individual trachea can require constant attention of the staff caring for these patients. Such conditions and problems can render the patentcy of the airway uncertain.

No less critical are the complications of prolonged tracheostomy. Such complications are tracheomalacia with progression to fistulae between the trachea and the esophagus, erosion of the anterior trachea and the innominate artery (often a fatal event), and later tracheal stenosis which sometimes necessitates surgical correction.

To solve the aforementioned problems and to make tracheostomy a safer modality of care, the present invention of a new tracheostomy tube has been developed. The present invention has four distinctive features. Those four distinctive features are a precision cuff fitted to each trachea, a flexible tube that will conform to any depth of the trachea within the neck, a self-locking clip that adjusts the tube securely to any neck regardless of the depth of the trachea, and a malleable but rigid obturator for ease of insertion.

The presision cuff is fitted to each trachea. The cuff of tracheostomy tubes of the prior art are not provided with this feature. Most tracheostomy tubes that are in use now and in the prior art have a soft cuff that, when inflated, assumes a fusiform shape presenting a narrow surface in contact with the trachea mucosa. Any prolonged pressure above twenty-five torr increases the risk of tracheal necrosis.

A more or less convoluted type or fluted cuff, with constricting bands to limit distention to the specific size of each trachea, is provided by the present invention. The average tracheal lumen size in the adult male is 25 mm and in the female 23 mm, with a standard deviation of 4 mm each way.

Accurate size of each trachea is determined, before the opening is made in the trachea. This is done by placing a marker of known size on the neck and then obtaining a radiograph and measuring the film to determine the tracheal lumen size in relation to the known size of the radiographed marker. Thus, each cuff used is the precise size for each trachea as ascertained by this measurement procedure.

The advatage of the precision convoluted-like or fluted cuff is to equalize the pressure over a longer segment of the mucosa by the use of the constricting bands limiting the size in the cuff constrictions. This also insures uniform diameter and controlled expansion.

The convoluted-like or fluted cuff and the manner of assuring the precise size in relation to the patient's trachea, effects a more complete seal at a lower pressure on the tracheal mucosa. Each convolution-like roll or flute creates a seal and the plurality of seals increases the total sealing effectiveness, thus avoiding the problem of the fusiform configuration which is inherent in the single chamber cuff.

It is to be noted that the precision cuff of the present invention has been described as convolution-like or fluted on the exterior surface. Note that it is not the same as a common corrugated configuration. The plurality of adjoining adjacent circular flutes interface with each other at the sides. The flutes are somewhat like convolutions or partial toroids upon adjacent toroids, better described as being fluted. The aforementioned constriction bands each are fitted into the crease between each two adjoining and adjacent flutes.

In the prior art, some attempt has been made to change the aforementioned fusiform configuration to a convolution-like arrangement. Actually the configuration taught in the prior art is more like a corrugated configuration. The corrugated-like configuration of the prior art is not the same as the closely fluted surface of the present invention and it does not accomplish the same objective, particularly it is to be noted that no constricting bands between flutes is taught in the prior art.

Some spiral reinforcement has also been taught in the prior art, but this is not the same as the constricting circular-like bands taught in the present invention. In the present invention, when the precision cuff is inflated to a predetermined low pressure, the constricting bands limit the outside diameter to the predetermined precision fit in the trachea. There is no such predetermination or limitation in the prior art.

In the Static Tracheostomy Tube the tube design remains constant at 8 mm inside diameter and the cuff size becomes the variable in selecting the tracheostomy device to be used in a given patient. This is a unique and novel feature not provided in the prior art.

It is to be understood that the aforementioned 8 mm inside diameter for the static tracheostomy tube of this invention is the preferred embodimetn, but that it may be varied either way without departing from the scope or intent of this invention.

The tracheostomy tube of this invention is flexible. The non-rigid contour and configuration will conform to any depth of the trachea within the neck. With the cuff inflated the non-rigid contour and configuration of the tracheostomy tube will always be in the center position of the lumen of the trachea.

By having the tracheostomy tube centered in the lumen of the trachea it avoids having the motion of the tip of the tube causing erosion of the anterior trachea and the adjacent innominate artery. In the like manner, the centering of the tracheostomy tube in the lumen of the trachea also avoids erosion posteriorly into the adjacent esophagus.

The flexible tracheostomy tube of this invention has a corrugated configuration. The corrugated configuration of the flexible tracheostomy tube absorbs and cushions the thrust created by the pulsations of the mechanical respirator. This absorbing and cushioning effect eliminates the abrasive motion of the tracheostomy tubes of the prior art to the trachea mucosa. Thus, the present invention allows long term respiratory support while decreasing the likelihood of fistulae. The corrugated configuration also prevents accidental kinking of the tube that would cut off the flow of air with disastrous results.

The present invention's self-locking clip adjusts the tracheostomy tube securely to any neck, regardless of the depth of the trachea, without displacing the tip of the tube from the central position within the lumen of the trachea.

A malleable, but rigid, obturator is provided for the Static Tracheostomy Tube for ease in insertion.

A plurality of sizes of the Static Tracheostomy Tube is provided in order to meet the needs for the range of diameters of the trachea that may be found in patients when making the precision fit by the aforementioned measurement procedure.

In addition to inserting the Static Tracheostomy Tube through an opening in the neck area, the tube can also be inserted into the trachea through the mouth or through the nose.

Regarding the flexible tube means it is to be noted that it is in a corrugated form of circular-like rings that provides for great flexibility and at the same time provides a means that will absorb the thrust of the pulsations of mechanical respiratory equipment connected to the tracheostomy tube. This configuration and shock absorbing characteristic is not present in the prior art.

In the prior art some attempt has been made to make the tubes flexible by using spiral reinforcement and by serating the outside surface. However, these steps are not the same as the corrugated like configuration of the present invention which is not only flexible, but also absorbs the thrust and pulsations of mechanical equipment connected to the tracheostomy tube.

It is, therefore, an object of the invention to provide a Static Tracheostomy Tube for a reliable airway for patients requiring mechanical assistance in breathing.

It is another object of the invention to provide a Static Tracheostomy Tube that avoids the complications of prolonged tracheostomy.

It is also an object of the invention to provide a Static Tracheostomy Tube that makes tracheostomy a safer modality of care.

It is still another object of the invention to provide a Static Tracheostomy Tube that has a precision cuff fitted to each trachea under treatment.

It is yet another object of the invention to provide a Static Tracheostomy Tube that has a flexible (but rigid) tube that will conform to any depth of the trachea within the neck of the patient.

It is yet still another object of the invention to provide a Static Tracheostomy Tube that has a self-locking clip that adjusts the tube securely to any neck, regardless of the depth of the trachea.

It is also still another object of the invention to provide a Static Tracheostomy Tube that has a malleable, but rigid, obturator for ease of insertion.

It is still another object of the invention to embody all of the features of this design into a endotracheal tube passed via the mouth or nose for use in conduction of gases used in anesthesia.

Further objects and advantages of the invention will become more apparent in the light of the following description of the preferred embodiments.

BRIEF DESCRIPTION OF THE DRAWINGS

FIG. 1 is a pictorial view of a tracheostomy tube inserted into the trachea through an opening in the neck of a patient;

FIG. 2 is an exploded side view of a tracheostomy tube and an obturator before insertion into a patient;

FIG. 3 is a side view of a tracheostomy tube inserted in an opening in the neck of a patient (shown in partial cross section), with the obturator removably inserted in the tracheostomy tube before removal;

FIG. 4 is a top view of a self-locking clip for a tracheostomy tube;

FIG. 5 is an exploded view of FIG. 4;

FIG. 6 is a pictorial view of FIG. 4 in position around a partial view of a tracheostomy tube;

FIG. 7 is an end view of the coupling end of a tracheostomy tube;

DESCRIPTION OF THE PREFERRED EMBODIMENTS

Figure 8:
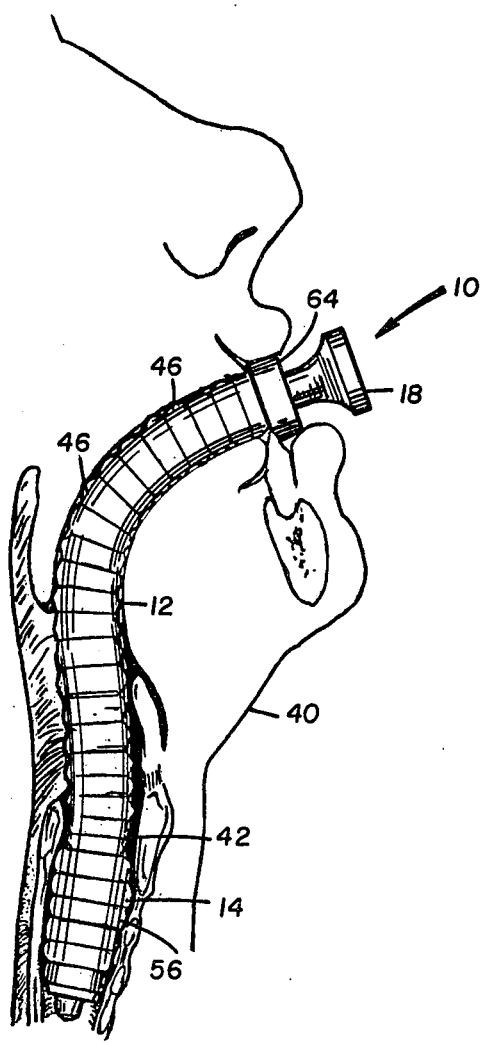
FIG. 8 is a partial pictorial side view of an alternative method of inserting a tracheostomy tube through the mouth instead of the neck.

Referring to the drawings and particularly to FIGS. 1, 2, 3, and 8, an improved Static Tracheostomy Tube is shown at 10.

The tracheostomy tube 10 consists of a flexible tube means 12, a precision cuff means 14, a self-locking clip means 16, and an obturator 18.

The tube means 12 is shown in the original straight configuration in FIG. 2 and in the more or less curved configuration when inserted in the trachea through an opening in the neck in FIG. 3.

The curved configuration of the flexible tube means 12 is obtained by inserting the obturator 18 into the flexible tube means 12 and then bending the two elements to the desired curved configuration for insertion into the trachea 42 of patient 40. The curved shape is maintained by the bent obturator 18 which is malleable to permit bending, but is rigid enough to maintain the curved configuration.

After the flexible tube means 12 of the tracheostomy tube 10 is inserted into the trachea and the precision cuff means 14 is inflated as hereinafter described, the obturator 18 is removed by withdrawing the obturator 18 from the flexible tube means 12.

The self-locking clip means 16 is placed around and adjusted to the flexible tube means 12 at a position that will properly secure the flexible tube means 12 at the neck 44 of patient 40. The self-locking clip means 16 locks in place when the pair of spring loaded latch means 20 are inserted into the latch pockets 22 and the latch means 20 snap and lock through the latch keeper pockets 24.

The self-locking clip means 16, secured around the flexible tube means 12 at the patient's neck, is held in position by suitable tie means 26 around the neck 44 of patient 40 and affixed to the male portion 28 and the female portion 30 of the self-locking clip means 16 through apertures 32 and 34 in portions 28 and 30 respectively.

When it is necessary to readjust the self-locking clip means 16 on the flexible tube means 12, or to remove it, the spring loaded latch means 20 are released by pressing latch release buttons 36 (one on each side for each spring loaded latch means 20). Depressing the latch release buttons 36 releases the spring loaded latch means 20 from the latch keeper pockets 24.

The self-locking clip means 16 has an aperture 38, formed half by male portion 28 and half by female portion 30, which encircles the flexible tube means 12. FIG. 4 shows the self-locking clip means 16 in assembled position, FIG. 5 shows the self-locking clip means 16 parted in order to assemble around the flexible tube means 12 as shown in FIG. 6. The tracheostomy tube 10 is shown in place, as described hereinbefore, on the neck 44 of patient 40 in FIG. 1.

The flexible tube means 12 is formed in a somewhat convolution manner with concentric corrugations 46 to maintain the tubular form, to provide for absorbing thrust, and to prevent kinking. The concentric corrugations 46 may be spaced from one end in the area at which the precision cuff means 14 is affixed to the flexible tube means 12.

As mentioned hereinbefore, the precision cuff means 14 is inflated during the procedure of inserting the flexible tube means 12 of the tracheostomy tube 10 in the trachea 42. The precision cuff means 14 surrounds the flexible tube means 12 in an encircling mode and is affixed to the flexible tube means 12 at the interface.

The precision cuff means 14 is inflated by attaching a syringe type means (not shown) to the valve inlet 48 of the inflating means 50 and then by operating the syringe type means to pump or force air into the inflating means reservoir 50. A check valve means 52 in the inflating means 50 at the valve inlet 48 prevents the air from escaping when the syringe type means is removed. The check valve can also be operated to permit the air to escape when the tracheostomy tube 10 is to be removed.

The air pumped or forced into the inflating means reservoir 50 passes down the inflating tube 54 to the inflatable precision cuff 14. The pressure of the inflating air fills out the precision cuff 14 so that it seals against the inside surface of the trachea 42 as shown in FIG. 3. Initially, the precision cuff 14 is in a collapsed or deflated form when the flexible tube means 12 is inserted in the trachea. The interior of the inflating tube 54 communicates with the interior of the inflating means reservoir 50 and the interior of the precision cuff 14. The inflating tube 54 may be affixed directly to a portion of the corrugation 46 of the flexible tube means 12 or retained in position by a plurality of eyelets 60 affixed to the several of the corrugations 46 as shown in FIGS. 2 and 3.

Precision cuff 14 is formed convoluted-like or fluted 56 on the outside and with a plurality of constricting bands 58 to limit the distention to the specific size of each trachea. The constricting bands 58 are located in the creased interface of each pair adjacent flutes or convolution-like folds. As noted hereinbefore, the required accurate size of the precision cuff 14 to be used in each case is determined, before the opening in the trachea 42 is made, by a radiograph and measuring process. The precision cuffs 14 are made in a plurality of sizes or diameters so that an exact precision fit unit can be selected for the trachea 42 in the patient 40 under care.

As noted hereinbefore, the advantage of the fluted 56 precision cuff 14 is to equalize the pressure over a longer segment of the mucosa by the use of the constricting bands 58 limiting the size of the cuff 14 and insuring a uniform diameter and a controlled expansion. This feature effects a more complete seal at lower pressure on the tracheal mucosa, with each flute 56 creating a seal and the plurality of such seals increasing the total sealing effectiveness. Thus, the present invention avoids the problem of the fusiform configuration of the single chamber cuff of the prior art.

The flexible tube means 12 has a coupling means 62 in the outboard collared end 64, as shown in FIG. 7, so that a mating coupling means on the connecting tube from a mechanical respirator can be easily connected or coupled to and disconnected or uncoupled from the tracheostomy tube 10 in the patient 40 to provide the respiratory care. If the patient 40 breathes on his or her own, the breathing can be accomplished through the internal passageway 66 through the flexible tube means 12 of the tracheostomy tube 10.

The obturator 18 has a malleable main shaft means 68, a grasping knob 70 on the outboard end, and a lead or guide nub 72 on the distal end to facilitate inserting the obturator into the internal passageway 66 in the flexible tube means 12. The obturator 18 may be constructed of separate elements or may be formed monolithically as a single piece.

As noted hereinbefore, the tracheostomy tube 10 may be inserted through an opening in the trachea 42, as described, or may be inserted through the nose (not illustrated) or through the mouth as shown in FIG. 8. The insertion and positioning procedure is substantially similar to that described for the opening in the trachea 42. When inserted through the mouth the outboard end of the flexible tube means 12 may also extend outside and away from the teeth and lips instead of as shown in FIG. 8.

As noted hereinbefore the present invention will always be in the center position of the lumen of the trachea 42 as shown in FIG. 3. This centered positioning avoids erosion by the tip of the tracheostomy tube 10 as occurs with the prior art devices.

Figure 9:
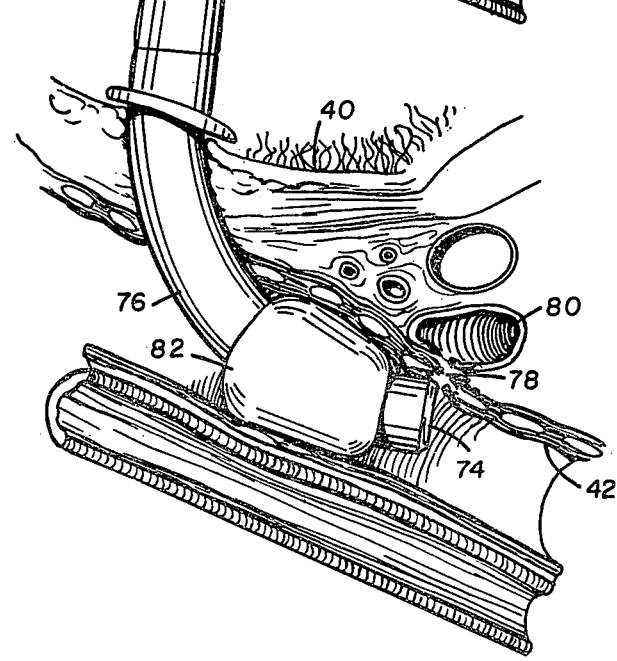
FIG. 9 is a partial pictorial side view of a tracheostomy tube of the prior art causing erosion of the anterior trachea and the adjacent innominant artery.

In FIG. 9 the tip 74 of a tracheostomy tube 76 of the prior art is seen eroding 78 the anterior trachea 42 and the adjacent innominate artery 80, of a patient 40. The fusiform cuff 82 of the tracheostomy tube 76 of the prior art is also seen in FIGS. 9 and 10.

Figure 10:
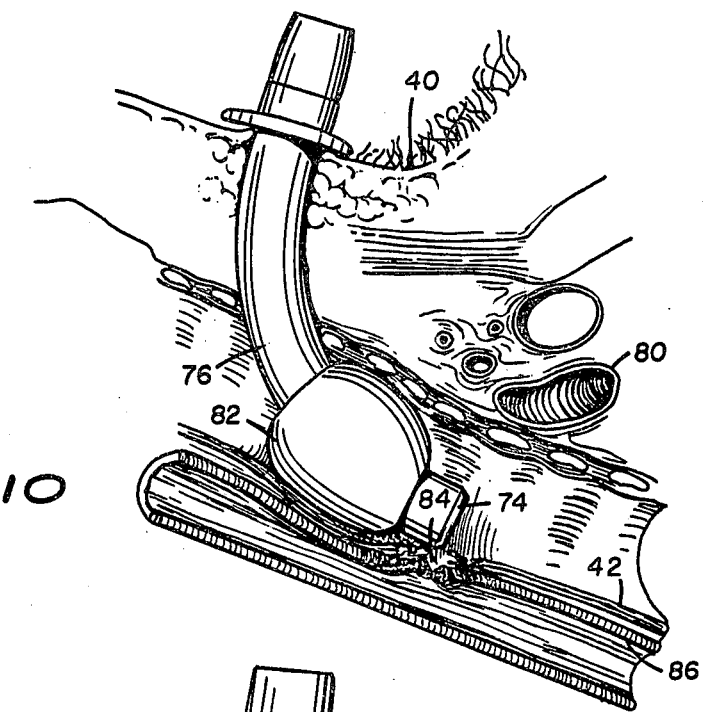
FIG. 10 is a partial pictorial side view of a tracheostomy tube of the prior art causing erosion of the posterior trachea and the adjacent esophagus.

Likewise, in FIG. 10, the tip 74 of a tracheostomy tube 76 of the prior art is seen eroding 84 the posterior wall of the trachea 42 and the adjacent esophagus 86.

Both of the aforementioned problems encountered with tracheostomy tubes of the prior art are extremely dangerous to patients undergoing respiratory care. The present invention avoids these problems. Also, as noted hereinbefore, the corrugated 46 flexible tube means 12 will absorb and cushion the thrust created by the pulsations of the respirator, thus eliminating the abrasive action and motion to the tracheal mucosa by the tracheostomy tubes of the prior art. This latter feature of the present invention permits long term respiratory support while decreasing the possibility of fistulae.

As can be readily understood from the foregoing description of the invention, the present structure can be configured in different modes to provide the ability to furnish respiratory care to a patient through a tracheostomy means.

Accordingly, modifications and variations to which the invention is susceptible may be practiced without departing from the scope and intent of the appended claims.

What is claimed is:

1. A portable closure means, comprising:

an inflatable cuff-like means, said inflatable cuff-like means being capable of being removably insertable within a pipe-like structure, said pipe-like structure having a flow passageway therethrough, said inflatable cuff-like means having a plurality of interfacing flutes, said plurality of interfacing flutes having a configuration of currugated-like convoluted rings located around the exterior periphery of said inflatable cuff-like means, said corrugated-like convoluted rings being adjoining and adjacent to each other in interface, said corrugated-like convoluted rings forming said flutes and providing a flexibility to prevent kinking;

a plurality of constricting bands, said constricting bands being located around said inflatable cuff-like means, each of said plurality of constricting bands being located individually in a respective crease of and between a pair of said adjoining and adjacent interfacing flutes; and an inflating means, said inflating means being connected to said inflatable cuff-like means and communicating internally therewith and therebetween, said inflatable cuff-like means being capable of internally closing said flow passageway through said pipe-like structure into which said inflatable cuff-like means has been removably inserted and subsequently inflated by said inflating means, said inflating means having an air inlet means, a check valve means, and an inflating tube-like means, said inlet means being a structure having a capability to receive and mate with the end of a pump means, said check valve means being located within said air inlet means, said check valve means becoming a part of said air inlet means structure, said inflating tube-like means being hollow and open ended, said inflating tube-like means having a first end and a second end, said first end of said inflating tube means being affixed to said air inlet means and communicating internally therewith, said second end of said inflating tube-like means being affixed to said inflatable cuff-like means and communicating internally therewith, the interior of said inflatable cuff-like means, said inflating tube-like means, and said air inlet means thereby communicating internally therethrough.

2. A closure means as recited in claim 1 and additionally, a pump means, said pump means being removably affixed to said air inlet means, said pump means being capable of inflating said cuff-like means through said inflating means.

3. A closure means as recited in claim 2, wherein said cuff-like means is capable of internally closing said flow passageway of said pipe-like structure and thereby controlling a flow of gaseous and liquid matter therethrough when said cuff-like means is inflated by the operation of said pump means.

4. A closure means as recited in claim 1 and additionally, an air reservior means, said air reservoir means having an inlet means and an outlet means, said air reservoir means being located and inserted between said air inlet means and said first end of said inflating tube-like means, said inlet means of said air reservoir means being affixed to said air inlet means and communicating internally therewith, said outlet means of said air reservoir means being affixed to said first end of said inflating tube-like means and communicating internally therewith.

5. A closure means as recited in claim 4, wherein said cuff-like means is capable of internally closing said flow passageway of said pipe-like structure and thereby controlling a flow of gaseous and liquid matter therethrough when said cuff-like means is inflated by the operation of said pump means.

6. A portable closure means, comprising:

an inflatable cuff-like means, said inflatable cuff-like means having a passageway therethrough, said inflatable cuff-like means being capable of being removably insertable within a pipe-like structure, said pipe-like structure having a flow passageway therethrough, said inflatable cuff-like means having a plurality of interfacing flutes, said plurality of interfacing flutes having a configuration of corrugated-like convoluted rings located around the exterior periphery of said inflatable cuff-like means, said corrugated-like convoluted rings being adjoining and adjacent to each other in interface, said corrugated-like convoluted rings forming said flutes and providing a flexibility to prevent kinking;

a plurality of constricting bands, said constricting bands being located around said inflatable cuff-like means, each of said plurality of constricting bands being located individually in a respective crease of and between a pair of said adjoining and adjacent interfacing flutes; and an inflating means, said inflating means being connected to said inflatable cuff-like means and communicating internally therewith and therebetween, said inflatable cuff-like means being capable of internally closing said flow passageway through said pipe-like structure into which said inflatable cuff-like means has been removably inserted and subsequently inflated by said inflating means, said inflating means having an air inlet means, a check valve means, and an inflating tube-like means, said inlet means being a structure having a capability to receive and mate with the end of a pump means, said check valve means being located within said air inlet means, said check valve means becoming a part of said air inlet means structure, said inflating tube-like means being hollow and open ended, said inflating tube-like means having a first end and a second end, said first end of said inflating tube means being affixed to said air inlet means and communicating internally therewith, said second end of said inflating tube-like means being affixed to said inflatable cuff-like means and communicating internally therewith, the interior of said inflatable cuff-like means, said inflating tube-like means, and said air inlet means thereby communicating internally therethrough; a flexible tube means, said flexible tube means having a first end and a second end and having an external surface, said flexible tube means having a flow passageway therethrough, said inflatable cuff-like means having an internal surface and being located on and around and thereby surrounding said flexible tube means, said first end of said flexible tube means projecting through said surrounding inflatable cuff-like means, said external surface of said flexible tube means being in adjacent interface with said internal surrounding surface of said inflatable cuff-like means and being affixed thereto, said second end of said flexible tube means being suitable for externally removably coupling and affixing flow control means thereto, said flow control means being capable of controlling gaseous and liquid matter flow through said flow passageway in said pipe-like structure when said inflatable cuff-like means is inflated by said inflating means while located and positioned within said flow passageway in said pipe-like structure.

* * * * *